United States Patent [19]

Jautelat et al.

[11] Patent Number: 5,252,582
[45] Date of Patent: Oct. 12, 1993

[54] MICROBIOCIDAL TRIAZOLO-PYRIDINE DERIVATIVES

[75] Inventors: Manfred Jautelat, Burscheid; Stefan Dutzmann, Hilden; Heinz-Wilhelm Dehne, Monheim, all of Fed. Rep. of Germany

[73] Assignee: Bayer Aktiengesellschaft, Leverkusen, Fed. Rep. of Germany

[21] Appl. No.: 15,701

[22] Filed: Feb. 9, 1993

[30] Foreign Application Priority Data

Feb. 18, 1992 [DE] Fed. Rep. of Germany ....... 4204816

[51] Int. Cl.$^5$ ................ A01N 43/90; C07D 471/04
[52] U.S. Cl. .................... 514/303; 546/119
[58] Field of Search .................... 546/119; 514/303

[56] References Cited

FOREIGN PATENT DOCUMENTS 0097425 5/1983 European Pat. Off. .

Primary Examiner—Bernard Dentz
Attorney, Agent, or Firm—Sprung Horn Kramer & Woods

[57] ABSTRACT

New triazolo-pyridine derivatives of the formula

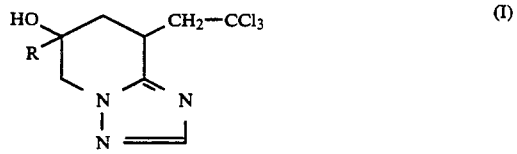

in which
R represents optionally substituted alkyl, optionally substituted cycloalkyl or optionally substituted aryl, and their acid addition salts and metal salt complexes, are outstandingly effective as microbicides in plant protection and in the preservation of materials.

10 Claims, No Drawings

MICROBIOCIDAL TRIAZOLO-PYRIDINE DERIVATIVES

The present invention relates to new triazolo-pyridine derivatives, to a process for their preparation, and to their use as microbiocides in plant protection and in the protection of materials.

It already been disclosed that certain dihalogenoalkyltriazolyl derivatives have fungicidal properties (cf. EP-OS (European Published Specification) 0,097,425). For example, 4-(2,4-dichloro-phenyl)-1,2-dibromo-4-hydroxy-5-(1,2,4-triazol-1-yl)-pent-1-ene and 4-(2,4-dichlorophenyl)-1,2-dichloro-4-hydroxy-5-(1,2,4-triazol-1-yl)pent-1-ene can be employed for combating fungi. The activity of these substances is good, but leaves something to be desired when low application rates are used.

New triazolo-pyridine derivatives of the formula

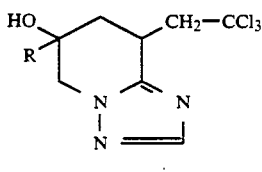

in which
R represents optionally substituted alkyl, optionally substituted cycloalkyl or optionally substituted aryl,
and their acid addition salts and metal salt complexes have now been found.

The compounds of the formula (I) contain at least one asymmetrically substituted carbon atom and can therefore be obtained in the forms of optical isomers. The present invention relates to the isomer mixtures as well as to the individual isomers.

Furthermore, it has been found that triazolo-pyridine derivatives of the formula (I) and their acid addition salts and metal salt complexes are obtained when triazolyl derivatives of the formula

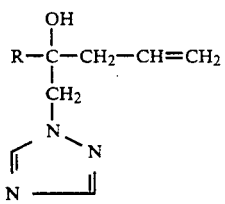

in which
R has the abovementioned meaning,
are reacted with carbon tetrachloride in the presence of a diluent under free-radical conditions and, if appropriate, an acid or a metal salt is subsequently subjected to an addition reaction with the resulting compounds of the formula (I).

Finally, it has been found that the new triazolo-pyridine derivatives of the formula (I) and their acid addition salts and metal salt complexes have very good microbicidal properties and can be used in plant protection as well as in the protection of materials.

Surprisingly, the substances according to the invention show a considerably better fungicidal activity than the previously known compounds of the same direction of action which have the most similar structure.

Formula (I) provides a general definition of the triazolo-pyridine derivatives according to the invention.

R preferably represents straight-chain or branched alkyl having 1 to 6 carbon atoms, it being possible for each of these radicals to be monosubstituted to trisubstituted by identical or different substituents from the series comprising halogen, cycloalkyl having 3 to 7 carbon atoms, phenyl and/or halogenophenyl, or represents cycloalkyl having 3 to 7 carbon atoms, it being possible for each of these cycloalkyl radicals to be monosubstituted to trisubstituted by identical or different substituents from the series comprising halogen and/or alkyl having 1 to 4 carbon atoms, or represents phenyl which can be monosubstituted to trisubstituted by identical or different substituents from the series comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano.

Particularly preferably,
R represents methyl, ethyl, n-propyl, isopropyl, n-butyl, tert.-pentyl, 1-ethyl1-methyl-propyl, 1,1-dimethyl-propyl or 1,1,2-trimethylpropyl, it being possible for each of these abovementioned radicals to be monosubstituted to trisubstituted by identical or different substituents from the series comprising fluorine, chlorine, bromine, phenyl, chlorophenyl, dichlorophenyl, fluorophenyl and/or difluorophenyl, or represents methyl-cyclohexyl, cyclohexyl, 1-fluorocyclopropyl, 1-chlorocyclopropyl, 1-methylcyclopropyl, cyclopropyl, 1-methylcyclopentyl, cyclopentyl or 1-ethyl-cyclopentyl, or represents phenyl which can be monosubstituted to trisubstituted by identical or different substituents from the series comprising fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano.

Other preferred substances according to the invention are addition products of acids and triazolo-pyridine derivatives of the formula (I) in which R has the meanings which have been mentioned above as being preferred or particularly preferred.

The acids which can be subjected to an addition reaction preferably include hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid, 1,5-naphthalenedisulphonic acid or camphorsulphonic acid, and also saccharin and thiosaccharin.

Preferred compounds according to the invention are furthermore addition products of acids of metals from main groups II to IV and sub-groups I and II as well as IV to VIII of the Periodic System of the Elements and triazolo-pyridine derivatives of the formula (I) in which R has the meanings which have been mentioned above as being preferred or particularly preferred. Particularly preferred here are the salts of copper, zinc, manganese, magnesium, tin, iron and nickel. Suitable anions of these salts are those which are derived from those acids which give physiologically acceptable addition products. Such acids which are particularly preferred in this context are the hydrohalic acids such as, for example, hydrochloric acid and hydrobromic acid, furthermore phosphoric acid, nitric and sulphuric acid.

Examples of substances according to the invention which may be mentioned are the triazolo-pyridine derivatives listed in the table below.

TABLE 1

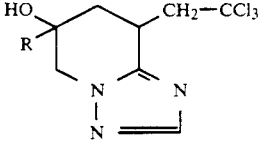

(I)

| R | R |
|---|---|
| —CH₃ | —C₃H₇-iso |
| —C₂H₅ | —C₄H₉-n |
| —C₃H₇-n | —C₄H₉-iso |
|  | —C₄H₉-sek. |

 

 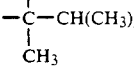

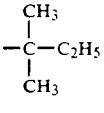 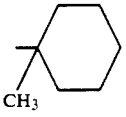

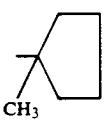 

 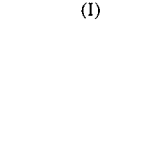

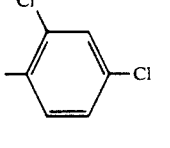

TABLE 1-continued

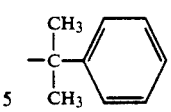

(I)

| R | R |
|---|---|
| 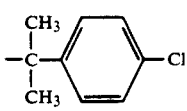 | 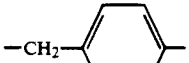 |
| 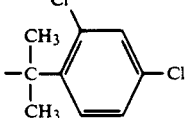 |  |
| 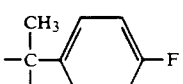 |  |
| 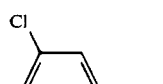 |  |
| 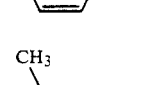 |  |
| 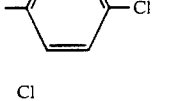 |  |
| 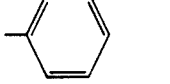 |  |
| 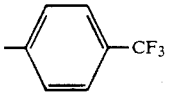 |  |
| 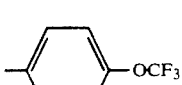 |  |
|  | 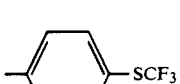 |

If 4-(1-chloro-cyclopropyl)-4-hydroxy-5-(1,2,4-triazol-1-yl)-pent-1-ene is used as starting substance, carbon tetrachloride as reactant and dibenzoyl peroxide as free-radical formers, then the course of the process according to the invention can be illustrated by the following equation:

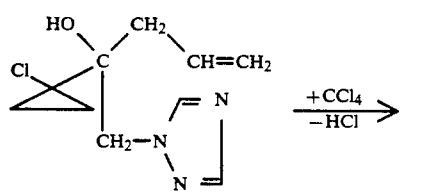
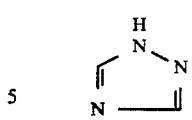

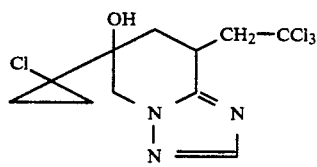

The triazolyl derivatives of the formula (II), which are required as starting substances for carrying out the process according to the invention, are known in some cases (cf. EP-OS (European Published Specification) 0,097,425). They can be prepared by a) reacting triazolylmethyl ketones of the formula

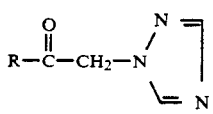  (III)

in which
R has the abovementioned meaning,
with allyl halides of the formula

CH$_2$=CH—CH$_2$—Hal    (IV)

in which
Hal represents chlorine or bromine,
in the presence of activated zinc, magnesium or aluminium and in the presence of a diluent, or b) reacting chloromethyl ketones of the formula

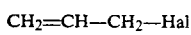  (V)

in which
R has the abovementioned meaning,
with allyl halides of the formula

CH$_2$=CH—CH$_2$—Hal    (IV)

in which
Hal has the abovementioned meaning,
in the presence of activated zinc, magnesium or activated aluminium and in the presence of a diluent, and the resulting hydroxyalkenes of the formula

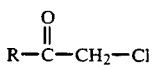  (VI)

in which
R has the abovementioned meaning,
are then reacted with 1,2,4-triazole of the formula

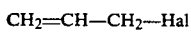  (VII)

in the presence of an acid-binding agent and in the presence of a diluent.

The triazolyl-methyl ketones of the formula (III), which are required as starting substances for carrying out process (a), are known or can be prepared in a simple manner by processes known in pinciple (cf. DE-OS (German Published Specification) 2,431,407 and EP-OS (European Published Specification) 0,353,558).

The allyl halides of the formula (IV) which are required as reactants for carrying out process (a) are known.

Suitable metals for carrying out the process (a) are activated zinc, magnesium or activated aluminium. The metals are employed in the process in the form of powder, shavings or flakes with addition of iodine as activator. Activated aluminium is prepared by adding catalytic amounts of mercury (II) chloride and iodine to aluminium flakes.

Suitable diluents for carrying out process (a) are all inert organic solvents which are customary for this type of reaction. The following are preferably suitable: ethers such as tetrahydrofuran, diethyl ether, dioxane, dimethoxyethane and diethylene glycol di-methyl ether (diglyme), and furthermore also aromatic hydrocarbons such as toluene, if appropriate in the form of a mixture with an ether.

When carrying out process (a), the reaction temperatures can varied within a certain range. In general, the process is carried out at temperatures between −20° C. and 80° C., preferably between 0° C. and +60° C.

Process (a) is generally carried out under atmospheric pressure. However, it is also possible to carry out the process under increased or reduced pressure.

When carrying out process (a), a procedure is followed in which an equimolar amount or else an excess of allyl halide of the formula (IV) and also an equimolar amount or else an excess of activated zinc, magnesium or aluminium together with a catalytic amount of mercury(II) chloride and iodine are employed per mole of triazolylmethyl ketone of the formula (III). The resulting products are isolated by customary methods. In general, a procedure is followed in which the reaction mixture is concentrated and treated with saturated aqueous ammonium chloride solution and with an organic solvent which is sparingly miscible with water, and the organic phase is separated off, dried and then concentrated.

The chloromethyl ketones of the formula (V), which are required as starting substances for carrying out process (b), are known or can be prepared by methods known in principle (cf. DE-OS (German Published Specification 3,049,461).

The first step of process (b) is carried out under the conditions which are also applied to process (a).

. The hydroxyalkenes of the formula (VI) can be further reacted directly with 1,2,4-triazole of the formula (VII). Alternatively however, they can first be converted into oxiranes and then reacted with 1,2,4-triazole of the formula (VII).

Suitable acid-binding agents for carrying out the second step of process (b) are all customary acid acceptors. The following can preferably be used: alkali metal carbonates and hydrogen carbonates such as sodium carbonate, potassium carbonate or sodium hydrogen carbonate, furthermore tertiary aliphatic or aromatic amines such as triethylamine, N,N-dimethyl-cyclohexyl-amine, N,N-dimethylbenzyl-amine and pyridine, and furthermore cyclic amines such as 1,5-diaza-bicyclo[4.3.0]non-5-ene (DBN), 1,8-diaza-bicyclo[5.4.0]undec-7-ene (DBU) and 1,4-diazabicyclo[2.2.2]octane (DABCO).

Suitable diluents for carrying out the second step of process (b) are all inert organic solvents. The following can preferably be used: aliphatic and aromatic, optionally halogenated hydrocarbons such as pentane, hexane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether as well as tert-butyl methyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, pyridine.

When carrying out the second step of process (b), the reaction temperatures can also be varied within a substantial range. In general, the process is carried out at temperatures between 0° C. and 200° C., preferably between 20° C. and 150°.

When carrying out the second step of process (b), a procedure is generally followed in which an equivalent amount, or else an excess, of 1,2,4-triazole of the formula (VII) and 2 to 3 mols of acid-binding agent are employed per mole of hydroxyalkene of the formula (VI). Working-up is carried out by customary methods.

Suitable free-radical formers for carrying out the process according to the invention are all substances which can customarily be used for such purposes. The following are preferably suitable: peroxides such as dibenzoyl peroxide, furthermore hydroperoxides such as tert.-butyl hydroperoxide, and furthermore azo-bis-isobutyronitrile. The process is expediently carried out under exposure to UV light.

Suitable diluents for carrying out the process according to the invention are all customary inert organic solvents. The following can preferably be used: cycloaliphatic or aromatic, optionally chlorinated hydrocarbons such as cyclohexane, benzene or chlorobenzene, and furthermore all chlorinated aliphatic hydrocarbons such as 1,2-dichloroethane or chloroform.

When carrying out the process according to the invention, the reaction temperatures can be varied within a substantial range. In general, the process is carried out at temperatures between 20° C. and 140° C., preferably between 40° C. and 120° C.

The process according to the invention is generally carried out under atmospheric pressure. However, it is also possible to carry out the process under increased pressure.

For carrying out the process according to the invention, at least an equimolar amount, but preferably an excess, of carbon tetrachloride and a catalytic amount of free-radical former are employed per mole of triazole derivative of the formula (II). Working-up is carried out by customary methods. In general, a procedure is followed in which the reaction mixture is concentrated, the residue which remains is treated with aqueous alkali metal carbonate solution and with an organic solvent which is sparingly miscible with water, and the organic phase is separated off, dried and then concentrated. If appropriate, the products obtained can be purified further by customary methods.

The triazolopyridine derivatives of the formula (I) according to the invention can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration and, if appropriate, purified by washing with an inert organic solvent.

Suitable substances for the preparation of metal salt complexes of the compounds of the formula (I) are preferably those salts of metals which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if appropriate, purified by recrystallisation.

The active compounds according to the invention have a powerful microbicidal action and can be employed in plant protection and in the protection of materials for combating undesired microorganisms, such as fungi and bacteria.

Fungicides are employed in plant protection for combating

Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus;* Puccinia species, such as *Puccinia recondite;* Tilletia species, such as *Tilletia caries;* Ustilago species, such as *Ustilago nuda* or *Ustilago avenae;*

Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* and *Pellicularia sasakii* on rice and for combating cereal diseases such as *Leptosphaeria nodorum, Cochliobolus sativus, Pyrenophora teres, Pseudocercosporella herpotrichoides,* as well as *Erysiphe* and *Fusarium* species. Moreover, the substances according to the invention show a very good action against Venturia, Sphaerotheca and Botrytis. Moreover, they have a good in-vitro action and also show acaricidal properties.

In the protection of materials, the substances according to the invention can be employed for protecting industrial materials against infestation with, and destruction by, undesired microorganisms.

Industrial materials in the present context are to be understood as meaning non-live materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infested with, or destroyed by, microorganisms. Parts of production plants, for example cooling water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heattransfer liquids, particularly preferably wood.

Microorganisms capable of bringing about degradation of, or change in, the industrial materials, which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophilla,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

The substances according to the invention can be converted to the customary formulations such as solutions, emulsions, suspensions, powders, foams, pastes, granules, aerosols, very fine capsules in polymeric substances and in coating composition for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

When used in plant protection the active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the substances according to the invention are used as fungicides, the application rate can be varied within a substantial range depending on the type of application. For example, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilograin of seed, preferably 0.01 to 10 g, are generally required. For the treatment of soil, active compound concentrations of 0.00001 to 0.1% by weight, preferably 0.0001 to 0.02% by weight, are required at the place of action.

The microbicidal agents used for the protection of industrial materials generally contain the active compounds in an amount from 1 to 95% by weight, preferably from 10 to 75% by weight.

When used in the protection of materials, the use concentrations of active compounds according to the invention depend on the species and the occurrence of the microorganisms to be combated and on the composition of the material to be protected. The best possible application rate can be determined by test series. In general, the use concentrations are in the range of from 0.001 to 5% by weight, preferably from 0.05 to 1.0% by weight, relative to the material to be protected.

When used in the protection of materials, the active compounds according to the invention can also be used as a mixture with other known active compounds.

Examples of active substances which may be mentioned are the following: benzyl alcohol mono(poly)-hemiformal and other formaldehyde-releasing compounds, benzimidazolyl methylcarbamate, tetramethylthiuram disulphide, zinc salts of dialkyl dithiocarbamates, 2,4,5,6-tetrachloroisophthalonitrile, thiazolylbenzimidazole, mercaptobenzthiozole, 2-thiocyanatomethylthiobenzthiazole, methylene bisthiocyanate, phenol derivatives such as 2-phenylphenol, (2,2'-dihydroxy-5,5'-dichloro)-diphenylmethane and 3-methyl-4-chloro-phenol, organs-tin compounds, trihalogenomethylthio compounds such as folpet, fluorfolpet, dichlorfluanid.

The preparation and the use of the active compounds according to the invention are illustrated by the following examples.

PREPARATION EXAMPLES

EXAMPLE 1

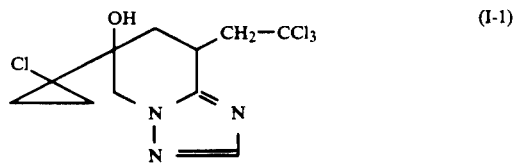

(I-1)

A mixture of 22.7 g (0.1 mol) of 4-(1-chloro-cyclopropyl)-4-hydroxy-5-(1,2,4-triazol-1-yl)-pent-1-ene, 200 ml of cyclohexane, 100 ml of carbon tetrachloride and 1 g of dibenzoyl peroxide is refluxed for 150 hours under irradiation with UV light. Then, the solvent and excess carbon tetrachloride are removed by distillation under atmospheric pressure. The residue which remains is treated with aqueous sodium carbonate solution and dichloromethane. The organic phase is separated off, dried over sodium sulphate and then concentrated under reduced pressure. The resulting crude product is chromatographed on silica gel using a mixture of hexane/ethyl acetate =1:1 as mobile phase. After concentration of the eluate, 9.6 g (28% of theory) of 7-(1-chloro-cyclopropyl)-7-hydroxy-5-(2,2,2-trichloroethyl)-5,6,7,8-tetrahydro-1,2,4-triazolo[2,3-a]-pyridine are obtained in the form of a solid substance of melting point 153° to 154° C.

Preparation of starting substances

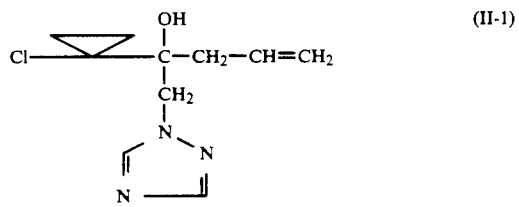

(II-1)

A solution of 12. 1 g (0.1 mol) of allyl bromide and 16.65 g (0.09 mol) of 1-(1-chlorocyclopropyl)-2-(1,2,4-triazol-1-yl)-ethan-1-one in 50 ml of tetrahydrofuran are added dropwise at 20° C. under nitrogen atmosphere in the course of 0.5 hours to a stirred mixture of 7.2 g (0.11 mol) of zinc dust, 0.1 g of iodine and 50 ml of absolute tetrahydrofuran. When the addition has ended, stirring is continued for 24 hours at room temperature, the mixture is then concentrated by stripping off the solvent and treated with aqueous ammonium chloride solution. The resulting mixture is extracted several times using dichloromethane. The combined organic phases are dried over sodium sulphate and then concentrated by stripping off the solvent under reduced pressure. In this manner, 10.2 g (50% of theory) of (4-(1-chloro-cyclopropyl)-4-hydroxy-5-(1,2,4-triazol1-yl)-pent-1-ene are obtained in the form of a solid substance of melting point 75° to 76° C.

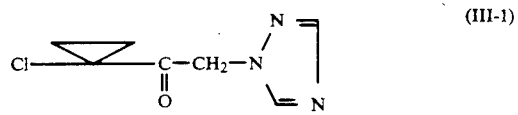

(III-1)

100 g (0.66 mol) of 1-chloro-cyclopropyl chloromethyl ketone in 80 ml of acetonitrile are added dropwise to a refluxing suspension of 83 g (0.6 mol) of potassium carbonate and 58 g (0.84 mol) of triazole in 330 ml of acetonitrile. The mixture is refluxed for 8 hours and then filtered off with suction and concentrated. The residue is taken up in ethyl acetate/toluene, and the mixture is washed with water, dried over sodium sulphate and concentrated. The subsequent purification by column chromatography in which dichloromethane was used as the mobile phase gave 62 g (51% of theory) of 1-(1-chlorocyclopropyl)-2-(1,2,4-triazol-1-yl)-ethan-1-one.

EXAMPLE 2

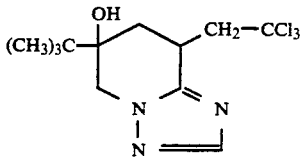 (I-2)

The compound of the formula (I-2) has been prepared according to the method disclosed in Example 1.
Melting point: 201°-203° C.

USE EXAMPLES

EXAMPLE A

Erysiphe test (barley)/protective
Solvent: 100 parts by weight of dimethylformide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

In this test, a degree of effectiveness of 100% at a concentration of 250 ppm in the spray liquor is shown by compound (I-1) according to the invention.

EXAMPLE B

Erysiphe test (barley)/curative
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f. sp. hordei*. 48 hours after the inoculation, the plants are sprayed with the preparation of active compound until dew-moist.

The plants are placed in a greenhouse at a temperature of about 20° C. and a relative atmospheric humidity of about 80%, in order to promote the development of mildew pustules.

Evaluation is carried out 7 days after the inoculation.

In this test, a degree of effectiveness of 100% at a concentration of 250 ppm in the spray liquor is shown by compound (I-1) according to the invention.

EXAMPLE C

Erysiphe test (wheat)/curative
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f. sp. tritici*. 48 hours after the inoculation, the plants are sprayed with the preparation of active compound until dew-moist.

The plants are placed in a greenhouse at a temperature of about 20° C. and a relative atmospheric humidity of about 80%, in order to promote the development of mildew pustules.

Evaluation is carried out 7 days after the inoculation.

In this test, a degree of effectiveness of 100% at a concentration of 250 ppm in the spray liquor is shown by compound (I-1) according to the invention.

EXAMPLE D

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, a degree of effectiveness of 100% at a concentration of 250 ppm in the spray liquor is shown by compound (I-1) according to the invention.

EXAMPLE E

Uncinula test (grapevine)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are sprayed with conidia of the fungus Uncinula necator.

The plants are subsequently placed in a greenhouse at 23° to 24° C. and at a relative atmospheric humidity of about 75%.

Evaluation is carried out 14 days after the inoculation.

In this test, a degree of effectiveness of 100% at a concentration of 10 ppm in the spray liquor is shown by compound (I-1) according to the invention.

EXAMPLE F

Venturia test (apple)/curative
Solvent: 4.7 parts by weight of acetone
Emulsifier: 0. 3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the pathogen causing apple scab (Venturia inaequalis). The plants remain in an incubation cabin at 20° C. and 100% relative atmospheric humidity for 1 day and are then placed in the greenhouse. After a predetermined number of hours, the plants are sprayed with the preparation of active compound until dripping wet.

The plants are placed in a greenhouse at a temperature of about 20° C. and a relative atmospheric humidity of about 70%.

Evaluation is carried out 12 days after the inoculation.

In this test, a degree of effectiveness of 100% at a concentration of 20 ppm in the spray liquor is shown by compound (I-1) according to the invention.

It will be understood that the specification and examples are illustrative but not limitative of the present invention and that other embodiments within the spirit and scope of the invention will suggest themselves to those skilled in the art.

What is claimed is:

1. A triazolo-pyridine derivative of the formula

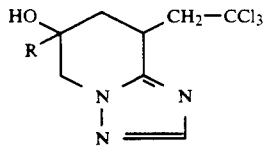

in which
R is alkyl, substituted alkyl, cycloalkyl, substituted cycloalkyl, aryl and substituted aryl,
or an addition product thereof with an acid or metal salt.

2. A triazolo-pyridine derivative according to claim 1, wherein
R is straight-chain or banched alkyl having 1 to 6 carbon atoms, monosubstituted to tri-substituted straight-chain or branched alkyl having 1 to 6 carbon atoms the substituents being identical or different and being selected from halogen, cycloalkyl having 3 to 7 carbon atoms, phenyl and halogenophenyl, or is cycloalkyl having 3 to 7 carbon atoms, monosubstituted to tri-substituted cycloalkyl having 3 to 7 carbon atoms the substituents being identical or different and being selected from halogen and alkyl having 1 to 4 carbon atoms, or is phenyl or monosubstituted to tri-substituted phenyl the substituents being identical or different and being selected from halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano.

3. A triazolo-pyridine derivative according to claim 1, wherein
R is methyl, ethyl, n-propyl, isopropyl, n-butyl, tert.-butyl, 1-ethyl-1-methyl-propyl, 1,1-dimethyl-propyl or 1,1,2-trimethylpropyl, or is, in each case monosubstituted to trisubstituted methyl, ethyl, n-propyl, isopropyl, n-butyl, 1-ethyl-1-methyl-propyl, 1,1-dimethylpropyl or 1,1,2-trimethylpropyl the substituents being identical or different and being selected from fluorine, chlorine, bromine, phenyl, chlorophenyl, dichlorophenyl, fluorophenyl and difluorophenyl, or is methylcyclohexyl, cyclohexyl, 1-fluorocyclopropyl, 1-chlorocyclopropyl, 1-methylcyclopropyl, cyclopropyl, 1-methylcyclopentyl, cyclopentyl or 1-ethyl-cyclopentyl, or is phenyl, or monosubstituted to trisubstituted phenyl the substituents being identical or different and being selected from fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and cyano.

4. A triazolo-pyridine derivative according to claim 1, wherein such compound is 7-(1-chloro-cyclopropyl)-7-hydroxy-5-(2,2,2-trichloro-ethyl)-5,6,7,8-tetrahydro-1,2,4-triazolo [2,3a]-pyridine of the formula

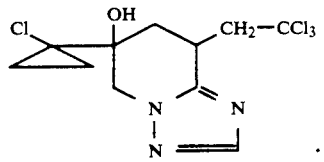

5. A triazolo-pyridine derivative according to claim 1, wherein such compound is 7-(1,1-dimethyl-ethyl)7-hydroxy-5-(2,2,2-trichloro-ethyl)-5,6,7,8-tetrahydro-1,2,4-triazolo-[2,3a]-pyridine of the formula

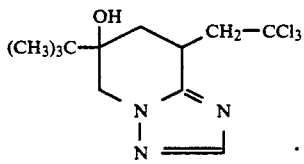

6. A microbiocidal composition comprising a microbicidally effective amount of a compound or addition product according to claim 1 and an inert diluent.

7. A fungicidal composition comprising a fungicidally effective amount of a compound or addition product according to claim 1 and an inert diluent.

8. A method of combating undesired microorganisms in plant protection and in the preservation of materials, which method comprises applying to such undesired microorganisms or to their habitat a microbicidally effective amount of a compound or addition product according to claim 1.

9. A method according to claim 8, wherein the undesired microorganisms are phytopathogenic fungi.

10. A method according to claim 8, wherein such compound is 7-(1-chloro-cyclopropyl)-7-hydroxy-5-(2,2,2-trichloroethyl)-5,6,7,8-tetrahydro-1,2,4-triazolo [2,3a]pyridine or 7-(1,1-dimethyl-ethyl)-7-hydroxy-5-(2,2,2-trichloroethyl)-5,6,7,8-tetrahydro-1,2,4-triazolo [2,3a]pyridine.

* * * * *